United States Patent [19]

Marchi et al.

[11] 4,179,438

[45] Dec. 18, 1979

[54] PROCESS FOR THE PREPARATION OF 3 IODO- AND 3 BROMORIFAMYCIN S

[75] Inventors: Egidio Marchi; Lauretta Montecchi, both of Bologna, Italy

[73] Assignee: Alfa Farmaceutici, S.p.A., Bologna, Italy

[21] Appl. No.: 957,844

[22] Filed: Nov. 6, 1978

[30] Foreign Application Priority Data

Nov. 29, 1977 [IT] Italy ................... 3620 A/77

[51] Int. Cl.$^2$ ............................. C07D 498/08
[52] U.S. Cl. ..................... 260/239.3 P; 424/244
[58] Field of Search .................. 260/239.3 P

[56] References Cited

FOREIGN PATENT DOCUMENTS 2548128  5/1976  Fed. Rep. of Germany .... 260/239.3 P

OTHER PUBLICATIONS

Dampier et al. "J. Am. Chem. Soc." vol. 98, No. 22, pp. 7064–7069 (1976)

Primary Examiner—Alan L. Rotman
Assistant Examiner—Robert T. Bond
Attorney, Agent, or Firm—Stevens, Davis, Miller & Mosher

[57] ABSTRACT

A process is disclosed for the preparation of 3 iodo-3 bromorifamycin S which consists in reacting rifamycin S with at least 2 equivalents of the corresponding halogen in the presence of at least one mole of pyridine for each equivalent of halogen. The reaction is carried out in inert, polar, hydrofillic solvents at a temperature not above the room temperature. The yields are very high and the products obtained have a high degree of purity.

5 Claims, No Drawings

PROCESS FOR THE PREPARATION OF 3 IODO- AND 3 BROMORIFAMYCIN S

DETAILED DESCRIPTION OF THE INVENTION

The present invention relates to an improved process for the preparation of 3 haloderivatives of Rifamycin S and particularly for the preparation of 3 iodo- and 3 bromorifamycin S.

The 3 halorifamycin S and SV are known (M. F. Dampier, C. W. Chen, H. W. Whitlock Jr.; Journ. of Am. Chem. Soc. 98:22 (October 1976) pages 7065–7066; M. F. Dampier H. W. Whitlock Jr. Journ of Am. Chem. Soc. 97:21 Oct. 15, 1975 pages 6254–56).

The process therein disclosed for the preparation of 3 iodorifamycin S consists in reacting one mole of rifamycin SV with one mole of elemental iodine in the solid state in the presence of pyridine and at a temperature of 25° C.

The reaction product is then treated with an aqueous solution of potassium ferricyanide and purified by passing it through a chromatographic column containing silica gel. The yield in purified 3 iodorifamycin S is 37%.

In the same article is disclosed the process for the preparation of 3 bromorifamycin S which consists in reacting one mole of rifamycin SV with 1.8 moles of pyridinium hydrobromide perbromide, in ethanol, at low tempeture. The reaction product is purified by chromatography through a column of silica gel.

The yield in purified 3 bromorifamycin S is 30%. 3 iodo- and 3 bromorifamycin S are transformed into 3 iodo- and 3 bromorifamycin SV respectively by treatment, in aqueous methanol 60%, with ascorbic acid.

The 3 haloderivatives of rifamycin S and SV are useful intermediates for the synthesis of derivatives of rifamycin S and SV having microbiological activity. However the low yields in 3 haloderivative obtainable with the known processes do not allow a practical industrial exploitation.

Object of the present invention is an improved process for the preparation of 3 iodo- and 3 bromorifamycin S which consists in reacting rifamycin S with at least 2 equivalents of an halogen selected from the group consisting of iodine and bromine per mole of rifamycin S, in the pesence of at least one mole of pyridine for each equivalent of halogen and in the presence of an inert polar and hydrophillic solvent at a temperature not above the room temperature.

The process of the present invention allows to obtain 3 iodo- and 3 bromorifamycin S in very high yields, in the order of 85–96% and even higher, and with a so high degree of purity to allow the direct use as intermediates in the preparation of derivatives, without requiring further purification.

It is however possible to subject the 3 iodo- and 3 bromorifamycins S obtained with the process of the present invention to a purification process such as, for instance, chromatography in a column of silica gel, as disclosed in the prior art, or crystallization from a suitable solvent.

In practising the present invention the amount of halogen may vary according to the type of halogen, the temperature and the solvent.

It has been noted, in fact, that in the case of iodine, satisfactory results are obtained with from 2 to 6 equivalents of halogen per mole of rifamycin S. The best results are obtained by using 4 equivalents of iodine. In the case of bromine satisfactory results are obtained when using from 2 to 4 equivalents of bromine per mole of rifamycin S. The best results are obtained with 3 equivalents to bromine.

The preferred amount of pyridine per equivalent of halogen, is in the case of bromine, one mole or a slight excess with reference to such an amount. In the case of iodine the preferred amount of pyridine is from 1 mole to 10 moles. In fact it has been noted that such an excess of pyridine, in the case of iodine, is not detrimental to the good course of the reaction.

The preferred reaction temperature is correlated to the type of the used halogen, to the weight ratios of the reactants and to the type and amount of the used solvent.

In the case of iodine the preferred temperature is around the room temperature whereas in the case of bromine it is within the range from $-10$ and $+15°$ C. with a further preference for the temperature around 0° C.

The solvents utilizable in practising the process of the present invention are inert, polar and hydrophillic solvents. Examples are: methanol, ethanol, dioxane, acetonitrile, dimethylformamide, tetrahydrofuran, dimethylsulfoxide, mixtures of the above solvents with water and, in the case of iodine, pyridine and aqueous pyridine.

The preferred solvents, in the case of iodine are methanol, ethanol and mixtures thereof with water; in the case of bromine are dioxane, methanol, ethanol and acetonitrile.

At the end of the reaction, it is necessary to eliminate the free halogen. In the case of iodine it is sufficient to bring the reaction mixture to dryness few times thereby the iodine sublimates.

In the case of bromine it is preferable to treat the reaction mixture with reducing agents in order to transform the elemental bromine into bromo ions which can be removed easily by means of washings. Among the reducing agents suitable for this purpose there are some (for instance alkaly metals thiosulfates in diluted aqueous solutions) which reduce only the bromine, leaving unchanged the formed 3 bromorifamycin S; others, on the contrary, (for instance ascorbic acid, sulfur dioxide) reduce also the 3 bromorifamycin S to 3 bromorifamycin SV. In the last case it is necessary to restore the form S by means of suitable oxidizing treatments (for instance manganese dioxide, potassium ferricyanide, ferric chloride, silver oxide, etc.).

The following examples are given for illustrating the present invention.

The thin layer chromatographies (TLC) therein mentioned have been carried out on layers of silica gel 60 $F_{254}$ 0.2 mm thick on aluminum plates (Merck).

The $R_{fR}$ values given for the products are referred to the $R_f$ of the rifamycin S.

EXAMPLE 1

Preparation of 3 iodiorifamycin S

In 8 ml pyridine (99 m.moles) are dissolved mg 508 (4 m. equiv.) at cool and under stirring. After 5 minutes mg 696 (1 m.mole) rifamycin S are added. After 40 minutes stirring at a temperature below 15° C., 200 ml chloroform are added. The organic layer is washed with aqueous hydrochloric acid 0.1 N and then with water. The organic layer is dried and brought to dryness. Chloroform is added and the solution is brought to dryness again. The operation is repeated many times to remove the iodine. The residue, dissolved in chloroform is treated with n-hexane obtaining a precipitate of 840 mg of raw material containing 700 mg of 3 iodorifamycin S (yield 85%). The raw product can be used directly as intermediate for further reactions. The product is purified by dissolving it in 3 ml of a mixture chloroform/methanol 40/1 (v/v) containing 0.1% (w/v) of oxalic acid, and passing through a chromatographic column of silica gel (O=2.5 cm height 20 cm). As eluent is used the same solvents mixture referred above.

The fractions containing an orange-brown product and which have on TLC a $R_{fR}=0.6$ (chloroform 40/methanol 1), corresponding to 3 iodorifamycin S, are collected, washed first with an acid solution then with water, finally dried and brought do dryness.

670 mg of pure 3 iodorifamycin S are obtained (yield 81.5%).

Minimal inhibiting concentrations (MIC):

| Staph. Aureus | 209 P | 0.1–0.25 |
|---|---|---|
| E. Coli | ML/35 | >50 |
| Klebsiella pne. | Ottaviani | 100 |

EXAMPLE 2

508 mg (4 m.equiv.) iodine are added, under stirring to 2 ml (25 m.moles) pyridine. After 5 minutes 8 ml ethanol, 696 mg rifamycin S (1 m.mole) and 3 ml water are added. After 40 minutes of stirring at room temperature 300 ml chloroform are added.

The chloroform solution is worked as described in Example 1 obtaining 825 mg of raw material containing 757 mg 3 iodorifamycin S (yield 92% of the theory).

The preparation has been repeated using ethylacetate instead of chloroform, thus obtaining a result (yield and degree of purity) practically equal to the proceeding one.

EXAMPLE 3

One works as Example 2. At the end of the reaction, instead of chloroform, 10 ml of a mixture methanol-water 70/30 (v/v) containing g 0.700 ascorbic acid are added. After 15 minutes stirring the solution is concentrated under vacuum to about one third of the original volume. 100 ml ethylacetate are added and the solution is washed repeatedly to remove the pyridine. The solution is dried on anhydrous sodium sulfate and brought to dryness obtaining 840 mg of product containing 740 mg of 3 iodorifamycin SV (yield 90%).

The product may be used for further reactions. For the transformation into the corresponding 3 iodorifamycin S the product is dissolved in an organic solvent, oxidized with manganese dioxide and purified as described in the preceeding examples.

EXAMPLE 4

Preparation of 3 bromorifamycin S g 2.39 (30 m.equiv.) bromine are added at −5° C. and under stirring to 2.37 g (30 m.moles) pyridine. After 5 minutes 150 ml ethanol and g 6.96 (10 m.moles) rifamycin S are added. After 15 minutes stirring at a temperature between −10° and 0° C. the reaction is stopped by adding 300 ml ethylacetate and washing the organic layer repeatedly with a solution 0.1 N of sodium thiosulfate up to the complete reduction of the bromine and then with a diluted acidic solution to remove the pyridine and finally with water. The organic layer is dried and brought to dryness.

The 3 bromorifamycin S is dissolved in chloroform and precipitated with n-hexane.

g 7.82 of raw product is obtained containing g 7.410 of 3 bromorifamycin S (yield 95%).

The raw product can be directly used as intermediate for further reactions.

The product can be purified by column chromatography on silica gel.

An analogous result is obtained by employing as solvent chloroform instead of ethylacetate.

Minimal inhibiting concentrations (MIC):

| Staph. Aureus | 209 P | 0.01 |
|---|---|---|
| E. Coli | ML 35 | 25–50 |
| Klebsiella pne. | Ottaviani | ≈50 |

EXAMPLE 5

One works as in Example 4. The reaction is stopped by adding g 5.28 (30 m.moles) of ascorbic acid dissolved in 100 ml methanol containing 30% water (v/v).

The solution is stirred for 10 minutes and concentrated under vacuum to one third of the initial volume. The residue is diluted with ethylacetate, and the organic phase is washed with aqueous hydrochloric acid 0.1 N and then with water, dried and brought to dryness and the residue is dissolved in chloroform and g 3.5 (40 m.mole) manganese dioxide (prepared according to the method of Rosenkrantz) are added.

After stirring for 15 minutes the dioxide is filtered off and the organic phase is washed with aqueous hydrochloric acid 0.1 N and then with water, dried and brought to dryness.

The residue, dissolved in chloroform, is precipitated with n-hexane.

The yield in 3 bromorifamycin S and its purity degree are similar to the ones obtained in example 4.

EXAMPLE 6

Working as in example 5 but using methanol as a reaction solvent instead of ethanol a yield of 95% has been obtained.

EXAMPLE 7

Working as in Example 5 but using dioxane as reaction solvent instead of methanol a yield of 85–90% has been obtained.

EXAMPLE 8

One works as in Example 5. The reaction is stopped by adding a saturated solution of sulphur dioxide in methanol in an amount sufficient to reduce the still present bromine and in the same time to reduce the 3 bromorifamycin S to 3 bromorifamycin SV. Stirring is carried out for 10 minutes. Proceeding as described at Example 5, substantially the same results are obtained.

EXAMPLE 9 g 27.8 (40 m.moles) rifamycin S suspended in 600 ml ethanol are added under stirring with g 9.6 (60 m.moles) bromine and g 4.90 (60 m.moles) pyridine. The reaction temperature is maintained at −10° C. Gradually the reactants dissolve and the suspension becomes a clear solution. After 30 minutes, g 20 ascorbic acid are added.

When the reduction of the 3 bromorifamycin S and of bromine in excess has been completed, 2500 ml ethylacetate are added and the solution is washed many times with water. The organic phase is then treated with 300 ml of an aquoeus solution of ferric chloride at 20% (w/w). After the oxidation of 3 bromorifamycin SV to 3 bromorifamycin S is completed, the phases are separated and the ethylacetate solution is washed repeatedly until neutrality, dried and brought to dryness.

The residue is crystallized from 60 ml of a mixture of glycolmonomethylether/water (4/1).

g. 26.5 of the pure crystallized product are obtained (yield 85.5%). Crystallization may also be carried out from ethylacetate.

We claim:

1. Improved process for the preparation of 3 iodo- and 3 bromorifamycin S characterized by the fact that rifamycin S is made to react with at least two equivalents of an halogen selected from the group consisting of iodine and bromine, per mole of rifamycin S in the presence of at least one mole of pyridine per each equivalent of halogen and in the presence of ethanol, methanol or mixtures thereof with water, operating at a temperature not above the room temperature.

2. Process according to claim 1 for the preparation of 3 iodorifamycin S characterized by the fact that are used from 2 to 6 equivalents of iodine per mole of rifamycin S, from 1 to 10 moles pyridine per equivalent of iodine and that the temperature is around the room temperature.

3. Process according to claim 2 characterized by the fact that 4 equivalents of iodine are used per mole of rifamycin S.

4. Process according to claim 1 for the preparation of 3 bromorifamycin S characterized by the fact that are used from 2 to 4 equivalents of bromine per mole of rifamycin S, 1 mole or a slight excess of pyridine per equivalent of bromine and that the temperature is comprised between $-10°$ and $+15°$ C. and preferably around $0°$ C.

5. Process according to claim 4 characterized by the fact that 3 equivalents of bromine are used per mole of rifamycin S.

UNITED STATES PATENT AND TRADEMARK OFFICE
CERTIFICATE OF CORRECTION

PATENT NO. : 4,179,438

DATED : December 18, 1979

INVENTOR(S) : Egidio MARCHI et al

It is certified that error appears in the above-identified patent and that said Letters Patent are hereby corrected as shown below:

Column 2, line 62, after "508" insert -- of iodine --.

Signed and Sealed this

Thirteenth Day of May 1980

[SEAL]

Attest:

SIDNEY A. DIAMOND

Attesting Officer

Commissioner of Patents and Trademarks